United States Patent [19]

Schmidt et al.

[11] 4,139,706
[45] Feb. 13, 1979

[54] NOVEL POLY(THIO)ETHERS HAVING TERMINAL AMINO GROUPS, A PROCESS FOR THEIR PRODUCTION AND THEIR APPLICATION

[75] Inventors: Oskar Schmidt, Kittsee; Walter Sibral, Tulln, both of Austria

[73] Assignee: Lim-Holding, S.A., Luxemburg, Luxembourg

[21] Appl. No.: 735,282

[22] Filed: Oct. 26, 1976

[30] Foreign Application Priority Data

Oct. 27, 1975 [AT] Austria .................. 8150/75
Oct. 27, 1975 [AT] Austria .................. 8151/75

[51] Int. Cl.² .......................... C07D 235/26
[52] U.S. Cl. ...................... 548/305; 528/354
[58] Field of Search .............. 548/305; 260/77.5 CH

[56] References Cited
U.S. PATENT DOCUMENTS

| 3,024,166 | 3/1962 | Kuna et al. | 548/305 |
|---|---|---|---|
| 3,920,683 | 11/1975 | Porret et al. | 548/305 |
| 3,928,377 | 12/1975 | Habermeier | 548/305 |
| 3,954,790 | 5/1976 | Habermeier | 548/305 |

FOREIGN PATENT DOCUMENTS 2453326  5/1975  Fed. Rep. of Germany .......... 548/305

OTHER PUBLICATIONS

Habermeier, Chem. Abst. 1976, vol. 84, No. 31905n.

Primary Examiner—Natalie Trousof
Attorney, Agent, or Firm—Beveridge, DeGrandi, Kline & Lunsford

[57] ABSTRACT

Poly(thio) ethers having terminal amino groups, said ethers having the formula:

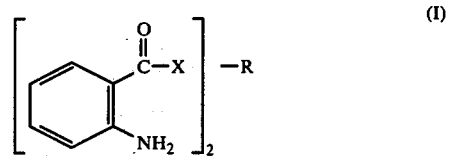

wherein X is oxygen or sulfur and R stands for a group of the formula

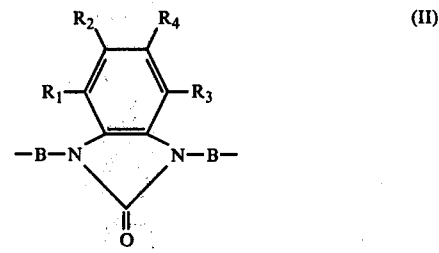

wherein $R_1$ to $R_4$ represent hydrogen or halogen and B stands for a divalent polyalkylene ether group or a polyalkylene thioether group or mixtures thereof such as is obtained by removal of the hydroxyl or mercapto groups from a polyalkylene ether diol or a polyalkylene thioether dithiol of a molecular weight of 100 to 15000. A process for the production and application is also disclosed. These ethers are used in the production of poly ureas having increased thermal stability and improved tensile and structural strength.

18 Claims, No Drawings

NOVEL POLY(THIO)ETHERS HAVING TERMINAL AMINO GROUPS, A PROCESS FOR THEIR PRODUCTION AND THEIR APPLICATION

It is known that polyureas possess a number of considerable advantages over polyurethanes of corresponding structure. Polyureas are obtained by reaction of polyisocyanates with polyamines. Suitable polyamines are particularly polyether polyamines of higher molecular weight. According to German Offenlegungsschrift No. 2 019 432, polyamines suitable for the production of such polyureas are obtained from aliphatic polyether polyols and isatic acid anhydride.

It was found that the use of poly(thio)ether diamines having at least one heterocyclic nucleus in their molecule (center) leads to the obtention of polyureas which are far superior to those known in respect of thermal stability and tensile and structural strength.

The invention relates to novel compounds having terminal amino groups, said novel compounds being of the general formula

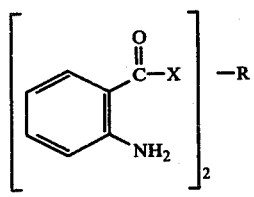

wherein X is oxygen or sulfur and R represents a group of the formula

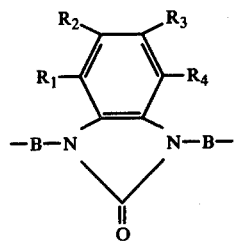

wherein $R_1$ to $R_4$ stand for hydrogen or halogen and B represents a divalent polyalkylene ether group or a polyalkylene thioether group such as it is obtained by removal of the hydroxyl or mercapto groups from a polyalkylene ether diol or a polyalkylene thioether dithiol of a molecular weight of 100 to 15000, in particular of 500 to 3000.

A further object of the invention is to provide a process for the production of the novel compounds of the formula I: These compounds are produced by heating a polyether diol or a polythioether dithiol of the formula III $R (XH)_2$  III wherein R and X have the meaning defined above, with at least two equivalents of isatic acid anhydride in the presence of strong bases to temperatures of 30° to 150° C., preferably of 45° to 130° C. The reaction can be carried out with or without the presence of inert solvents. The amount of catalyst used can be varied within a wide range. Preferably, 1 to 10 parts by weight of the alkaline compound per 100 parts by weight of isatic acid anhydride are used. The reaction is completed as soon as gas development ceases. The catalyst and excess isatic acid anhydride are filtered off, optionally after addition of an inert solvent, and the final product is obtained with a high degree of purity after treatment with $CO_2$, shaking with water and drying in vacuo under stirring. For the majority of application purposes, simple filtration of the amino polyether under pressure suffices.

Suitable starting materials for the process according to the invention are polyether diols of the formula III of a molecular weight of about 300 to 15000, preferably about 1000 to 10000 which are obtained by reaction of tetrahydrofurane or of tetrahydrofurane and ethylene oxide or of tetrahydrofurane and propylene oxide with a compound corresponding to the group R of the formula II wherein B is hydrogen, $CH_2CH_2OH$ or $CH_2CH(CH_3)OH$.

Preferred are compounds of the general formula I, or the production of these compounds, wherein R represents a group of the formula

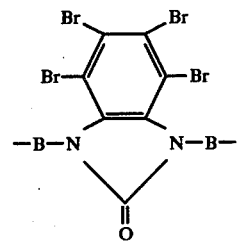

wherein B has the meaning defined above.

Further compounds favourable in respect of their application are such diamines of the formula I wherein B stands for a polyethylene ether group, a polypropylene ether group or a polyalkylene ether group containing ethylene ether groups and propylene ether groups in any given sequence. B can further represent a group containing ether groups as well as thioether groups.

In view of inexpensive starting materials, compounds of the formula I, or the production thereof, are favourable wherein B stands for a polyalkylene ether group derived from tetrahydrofurane, a polyalkylene ether group containing ethylene ether groups and alkylene ether groups derived from tetrahydrofurane in any given sequence or a polyalkylene ether group containing alkylene ether groups derived from tetrahydrofurane and propylene ether groups, in any given sequence.

Typical examples for the new compounds of the formula I according to the present invention and obtainable according to the process of the invention are the following:

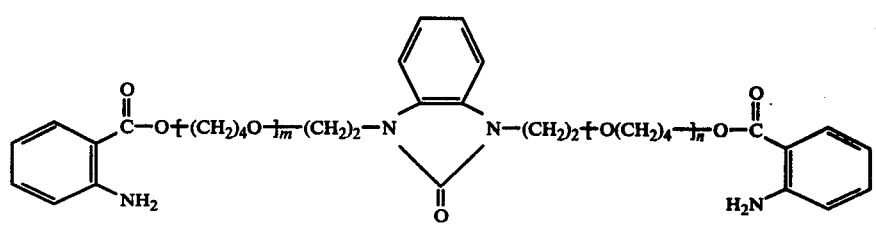
(1)
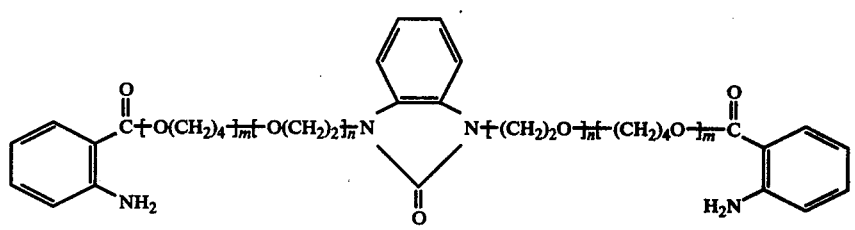
(2)
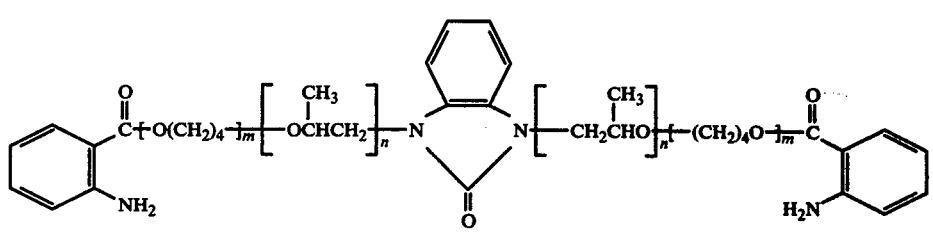
(3)
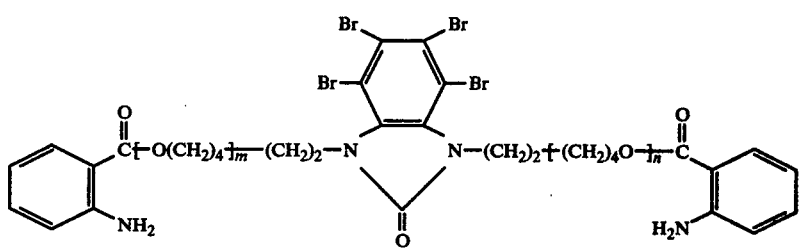
(4)
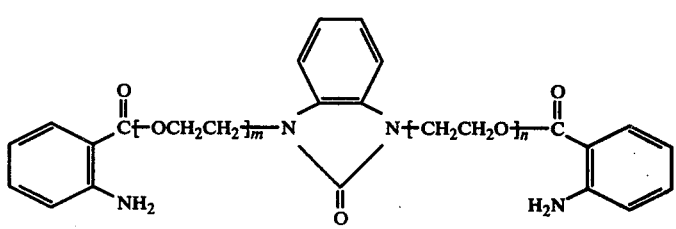
(5)
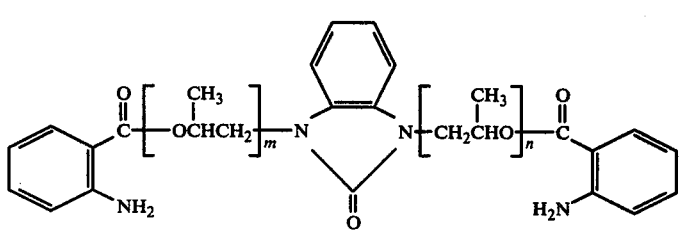
(6)
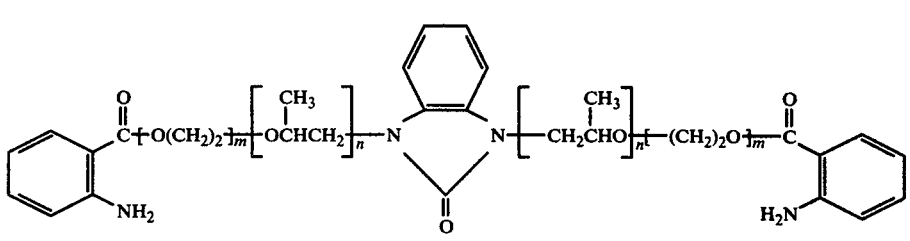
(7)

-continued

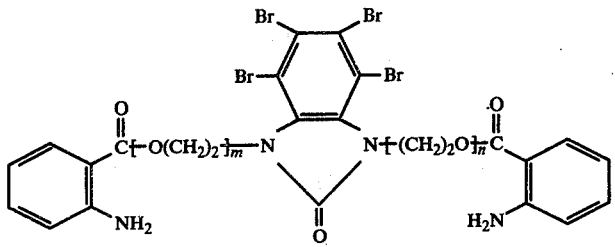

(8)

In these formulae and in the formulae contained in the Examples, the indices m and n in each case represent such integers that molecular weights of about 500 to 15000 are obtained in the compounds.

A further object of the invention is the application of the diamines of the general formula I as reactants with polyisocyanate in the production of plastic materials according to the isocyanate polyaddition process.

The production of plastic materials from the new compounds according to the invention or produced according to the invention in the isocyanate polyaddition process can be effected in any given manner conventional in polyurethane chemistry, i.e. employed in the reaction of polyhydroxyl compounds with polyisocyanates. This means that the reaction of the new compounds with polyisocyanates can be carried out in the presence of all the additives known in polyurethane chemistry, such as catalysts, flame-retarding substances, and the like.

In the production of plastic materials in the form of elastomers with a high modulus of elasticity, the polyadducts have preferably been obtained up to now in the presence of low molecular aromatic diamines as chain extenders. Since these diamines are carcinogenic, their use is encountering objections of a physiological nature. When employing the compounds according to the invention, the use of low molecular aromatic diamines can be completely omitted in the production of elastomeric plastic materials of high modulus of elasticity, so that the hazard of employing carcinogenic substances is eliminated.

Suitable polyisocyanates for the production of polyadducts emploing the new compounds of the present invention are all polyisocyanates known in polyurethane chemistry, i.e., for instance, tetramethylene diisocyanate, hexamethylene diosocyanate, 2,4-diisocyanatotoluene, 2,4-diisocyanatotoluene, mixtures of these isomers, 4,4-diisocyanato diphenyl methane or the like.

As already mentioned, the polyadducts produced under application of the new compounds according to the invention possess considerable advantages over polyurethanes of corresponding structure, particularly high stability, abrasion and wear resistance and thermal stability, as well as elasticity.

The production of the compounds of the formula I is described in the following by means of Examples:

EXAMPLE 1

108.6 g (0.1 mol) of a compound of the formula

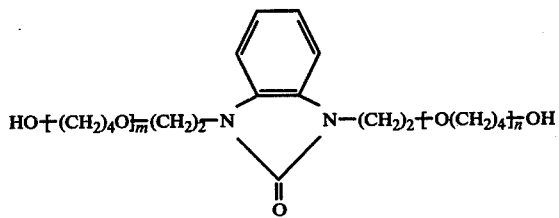

wherein m and n are integers, 35.9 g (0.22 mol) of isatic acid anhydride and 2.5 g powdered sodium hydroxide are heated for 3 hours to 75° C. and then briefly to 110° C. After cooling, 150 ml methylene chloride are added and the mixture obtained is filtered. For complete removal of the sodium hydroxide, 200 ml water are added to the filtrate and $CO_2$ is introduced. After three extractions with 200 ml water each, the organic phase is concentrated in vacuo. This procedure yields 123.2 g (93% of the theory, which means that 93% of all OH-groups have reacted with isatic acid anhydride) of a honey-coloured, viscous substance.

Amine titration: for 2.7358 g substance: 41.5 ml 0.1 n $HClO_4$ in glacial acetic acod.

EXAMPLE 2

117.4 g (0.1 mol) of a compound of the formula

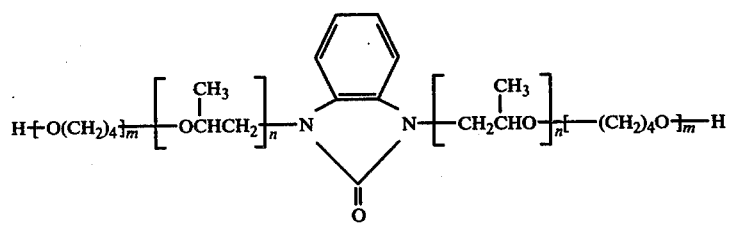

wherein m and n are integers, 35.9 g (0.22 mol) of isatic acid anhydride and 2 g powdered sodium hydroxide are heated for 3 hours to 80° C. and for 30 minutes to 110° C. and the mixture obtained is treated in analogy to Example 1. This procedure yields 138.6 g (96% of the theory) of a honey-coloured, viscous substance.

Amine titration: for 1.5732 g substance: 23.2 ml 0.1 n $HCLO_4$ in glacial acetic acid.

EXAMPLE 3

154.5 g (0.1 mol) of a compound of the formula

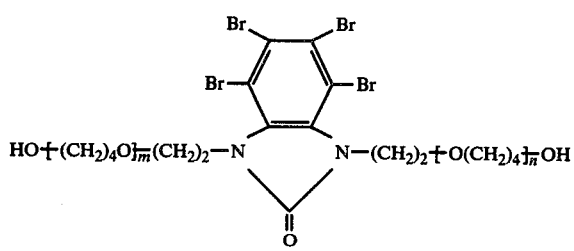

wherein m and n are integers, 35.9 g (0.22 mol) of isatic acid anhydride and 2.5 g powdered sodium hydroxide are heated for 4 hours to 75° C. and for 15 minutes to 110° C. and the mixture thus obtained is treated in analogy to Example 1. The yield amounts to 166.0 g (93% of the theory) of a honey-coloured, viscous substance.

Amine titration: for 1.3474 g substance: 15.3 ml 0.1 n $HClO_4$ in glacial acetic acid.

EXAMPLE 4

127.8 g (0.1 mol) of a compound of the formula

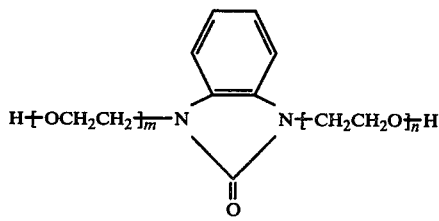

wherein m and n are integers, 36 g of isatic acid anhydride and 2.5 g powdered sodium hydroxide are heated for 3 hours to 75° C. and for 15 minutes to 110° C. After cooling, 150 ml methylene chloride are added and the mixture is filtered. For complete removal of the sodium hydroxide, 200 ml water are added and $CO_2$ is introduced. After three extractions with 200 ml water each, the organic phase is concentrated in vacuo. This procedure yields 142.5 g (94% of the theory) of a honey-coloured, viscous substance.

Amine titration: for 1.8452 g substance: 24.5 ml 0.1 n $HClO_4$ in glacial acetic acid.

EXAMPLE 5

106.2 g (0.1 mol) of a compound of the formula

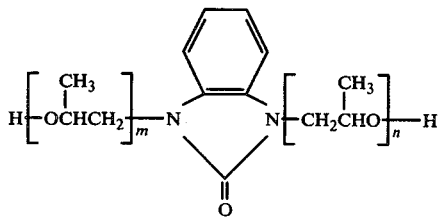

wherein m and n are integers, 35.9 g of isatic acid anhydride and 3.0 g powdered sodium hydroxide are heated for 3 hours to 90° C. and for 15 minutes to 110° C. and the mixture is treated according to Example 4. This procedure yields 118.3 g (91% of the theory) of a honey-coloured, viscous substance.

Amine titration: for 2.2463 g substance: 34.7 ml 0.1 n $HClO_4$ in glacial acetic acid.

EXAMPLE 6

177 g (0.1 mol) of a compound of the formula

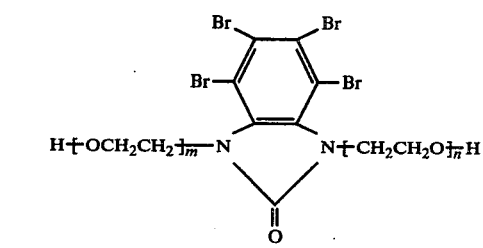

wherein m and n are integers, 35.9 of isatic acid anhydride and 2.0 g powdered sodium hydroxide are heated for 3 hours to 75° C. and for 1 hour to 110° C. and the mixture obtained is treated according to Example 4. This procedure yields 188.8 g (94% of the theory) of a honey-coloured, viscous substance.

Amine titration: 1.2653 g substance: 12.7 ml 0.1 n $HClO_4$ in glacial acetic acid.

EXAMPLE 7

96.6 g (0.1 mol) of a compound of the formula

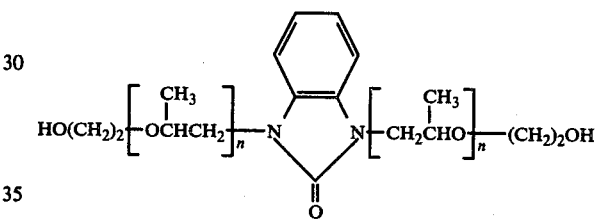

wherein n is an integer, 35.9 g of isatic acid anhydride and 10.0 g powdered sodium hydroxide are heated for 4 hours to 80° C. and then for 1 hour to 110° C. and treated in analogy to Example 4. This procedure yields 898 g (88% of the theory) of a honey-coloured, viscous substance.

Amine titration: for 6.9415 g substance: 12.2 ml 0.1 n $HClO_4$ in glacial acetic acid (89.7% of the theory), which means that 89.7% of all OH-groups have reacted with isatic acid anhydride.

The application of the compounds of the formula I is explained in detail by means of the following Examples:

EXAMPLE 8

264.8 g (0.2 mol) of the compound produced in Example 1 and 37 g toluylene diisocyanate (80% 2,4-isomer, 20% 2,6-isomer) are mixed, poured into a mould and then first heated to 60° C. for 30 minutes and then to 100° C. for 24 hours. This yields an elastomer of excellent mechanical properties.

Tensile strength: 280 kp $cm^{-2}$.
Structural strength: 45 kp $cm^{-1}$.
Shore hardness DIN 53505 50.

EXAMPLE 9

288.8 g (0.2 mol) of the compound aproduced according to Example 2 and 37 g toluylene diisocyanate are heated in a mould for for 30 minutes to 60° C. and then for 24 hours to 100° C. This yields an elastomer of excellent mechanical properties.

Tensile strength: 260 kp $cm^{-2}$.

Structural strength: 48 kp cm$^{-1}$.
Shore hardness DIN 53505 56.

EXAMPLE 10

151.6 g (0.1 mol) of the compound produced according to Example 4 and 18.5 g toluylene diisocyanate (80% 2,4-isomer, 20% 2,6-isomer) are mixed, poured into a mould and then heated for 1 hour to 60° C. and for 24 hours to 100° C. This yields an elastomer of excellent mechanical properties.
Tensile strength: 280 kp cm$^{-2}$.
Structural strength: 48 kp cm$^{-1}$.
Shore hardness DIN 53505: 52.

EXAMPLE 11

130 g (0.1 mol) of the compound produced according to Example 5 and 18.5 g toluylene diisocyanate are heated in a mould first for 30 minutes to 60° C. and then for 24 hours to 100° C. This yields an leastomer of the following physical data:
Tensile strength: 270 kp cm$^{-2}$.
Structural strength: 46 kp cm$^{-1}$.
Shore hardness DIN 53505: 54.

EXAMPLE 12

200.1 g (0.132 mol) of the compound produced according to Example 4 are reacted at 60 - 70° C. with 37 g toluylene diisocyanate. After 15 minutes, the temperature is raised to 90° C. under water jet vacuum. At this temperature, 11.8 g melted 1,4-dichloro-3,5-diaminobenzene are added and the mixture is poured into a preheated mould. An elastomer of excellent mechanical properties is obtained.
Tensile strength: 300 kp cm$^{-2}$.
Structural strength: 42 kp cm$^{-1}$.
Shore hardness DIN 53505 50.

EXAMPLE 13

130 g (0.1 mol) of the compound produced according to Example 5 to which 42.5 g (0.245 mol) toluylene diisocyanate (80% 2,4-isomer, 20% 2,6-isomer) have been added are stirred for 1 hour at a temperature of 50–60° C.
Then, the temperature is raised to 90° C., 22.9 g 1,4-dichloro-3,5-diaminobenzene are added and the mixture is poured into a mould. It is heated for 24 hours and this procedure yields an elastomer of the following properties:
Tensile strength: 240 kp cm$^{-2}$.
Structural strength: 42 kp cm$^{-1}$.
Shore hardness DIN 53505: 50.

EXAMPLE 14

130 g (0.1 mol) of the diamine produced according to Example 5, to which 61.25 g (0.245 mol) of 4,4-diisocyanate diphenyl methane have been added, are stirred for 1 hour at a temperature of 50 - 60° C. Then the temperature is raised to 90° C., 22.9 g of 1,4-dichloro-3,5-diaminobenzene are added and the mixture is poured into a mould. After heating for 24 hours, an elastomer of the following properties is obtained:
Tensile strength: 380 kp cm$^{-2}$.
Structural strength: 58 kp cm$^{-1}$.
Shore hardness DIN 53505: 55.

(6)
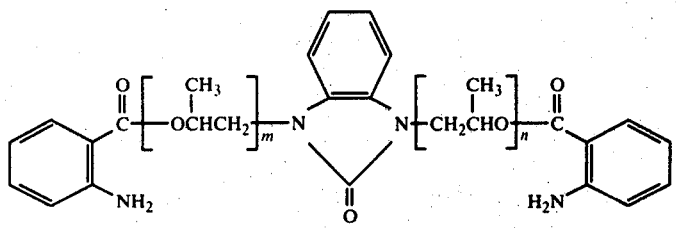
17. A compound according to claim 1, represented by the formula (7)
18. A compound according to claim 1, represented by the formula (8)
(7)
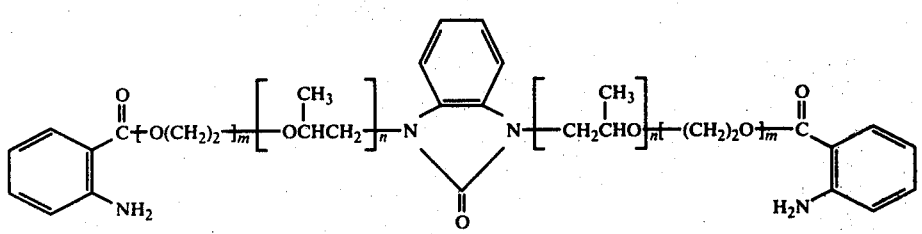
(8)
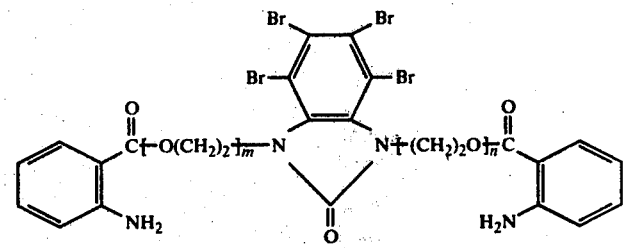

What we claim is:

1. A compound having terminal amino groups, said compound being of the formula

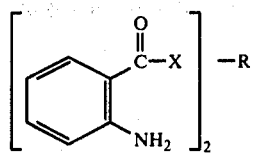

wherein X is oxygen or sulfur and R stands for a group of the formula

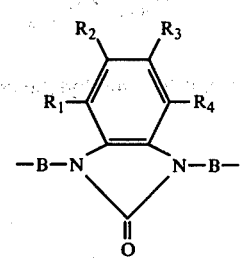

wherein $R_1$ to $R_4$ represent hydrogen or halogen and B stands for a divalent polyloweralkylene ether group or a polyloweralkylene thioether group or mixtures thereof such as it is obtained by removal of the hydroxyl or mercapto groups from a polyloweralkylene ether diol or a polyloweralkylene thioether dithiol of a molecular weight of 100 to 15000.

2. A compound according to claim 1, wherein B stands for a divalent polyloweralkylene ether group or a polyloweralkylene thioether group such as it is obtained by removal of the hydroxyl or mercapto groups from a polyloweralkylene ether diol or a polyloweralkylene thioether dithiol of a molecular weight of 500 to 3000.

3. A compound according to claim 1, wherein R represents a group of the formula

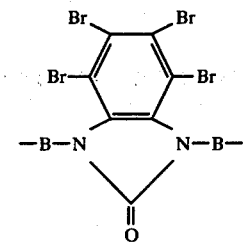

wherein B stands for a divalent polyloweralkylene ether group or a polyloweralkylene thioether group such as it is obtained by removal of the hydroxyl or mercapto groups from a polyloweralkylene ether diol or a polyloweralkylene thioether dithiol of a molecular weight of 100 to 15000.

4. A compound according to claim 1, wherein B represents a polyethylene ether group.

5. A compound according to claim 1, wherein B represents a polypropylene ether group.

6. A compound according to claim 1, wherein B represents a polyloweralkylene ether group containing ethylene ether groups and propylene ether groups in any given sequence.

7. A compound according to claim 1, wherein B represents a group containing ether groups as well as thioether groups.

8. A compound according to claim 1, wherein B represents tetramethylene ether.

9. A compound according to claim 1, wherein B represents a polyloweralkylene ether group containing ethylene ether groups and tetramethylene ether, in any given sequence.

10. A compound according to claim 1, wherein B represents a polyloweralkylene ether group containing tetramethylene ether groups and propylene ether groups, in any given sequence.

11. A compound according to claim 1, represented by the formula (1)

12. A compound according to claim 1, represented by the formula (2)

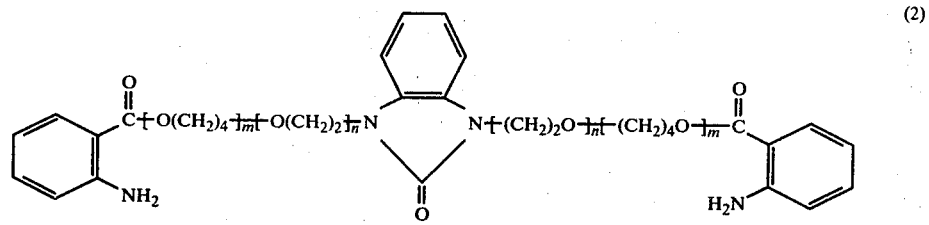

(2)

13. A compound according to claim 1, represented by the formula (3)

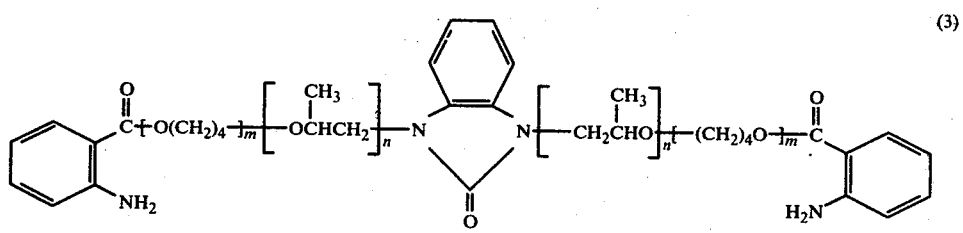

(3)

14. A compound according to claim 1, represented by the formula (4)

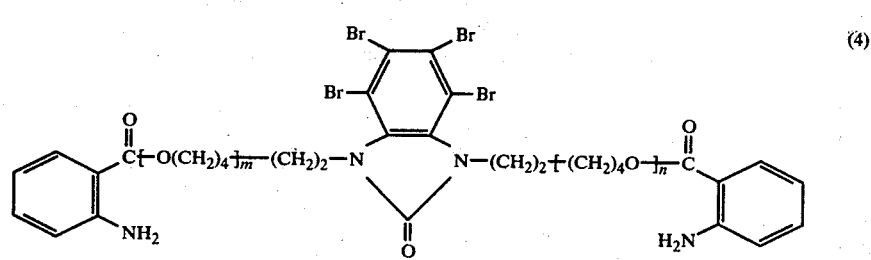

(4)

15. A compound according to claim 1, represented by the formula (5)

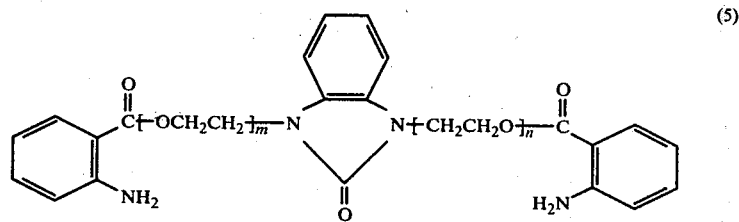

(5)

16. A compound according to claim 1, represented by the formula (6)

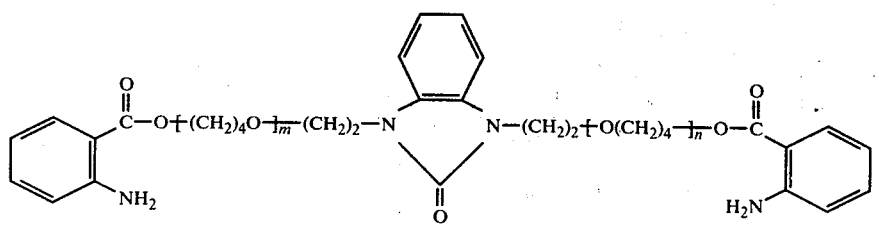

(1)